United States Patent [19]

Mohr et al.

[11] Patent Number: 4,979,823
[45] Date of Patent: Dec. 25, 1990

[54] METHOD AND ARRANGEMENT FOR BACKGROUND COMPENSATION IN MATERIAL ANALYSIS

[75] Inventors: Joachim Mohr; Felix Kerstan, both of Jena, German Democratic Rep.

[73] Assignee: Jenoptik Jena GmbH, Jena, Fed. Rep. of Germany

[21] Appl. No.: 267,050

[22] Filed: Nov. 4, 1988

[30] Foreign Application Priority Data
Jan. 20, 1988 [DE] Fed. Rep. of Germany ....... 3123036

[51] Int. Cl.$^5$ ..................... G01J 3/433; G01N 21/74
[52] U.S. Cl. .................................... 356/307; 356/311; 356/312
[58] Field of Search ........................ 356/307, 312, 311

[56] References Cited

U.S. PATENT DOCUMENTS 4,318,614  3/1982  Falk et al. .................. 356/311
4,534,646  8/1985  Tamm et al. ................ 356/312

FOREIGN PATENT DOCUMENTS 3600943  10/1986  Fed. Rep. of Germany .

Primary Examiner—Vincent P. McGraw
Attorney, Agent, or Firm—Jordan and Hamburg

[57] ABSTRACT

In a background compensation in material analysis, the value of the background signal is separated from the value of a gross analyte signal generated by athermal radiation excitation after thermal excitation. The thermal atomization takes place in a stepwise manner by stepwise heating and each step is divided into a first part for the measurement of the gross analyte signal and a second part for the measurement of the background signal.

5 Claims, 2 Drawing Sheets

METHOD AND ARRANGEMENT FOR BACKGROUND COMPENSATION IN MATERIAL ANALYSIS

The invention relates to a method for background compensation in material analysis, in which the value of the background signal is separated from the value of a gross signal of the analyte (i.e. substance to be analyzed), said gross signal being generated after thermal atomization of the analyte residue by athermal excitation.

Optical atomic spectroscopy with electrothermal atomization has the advantage that a high absolute and relative detection sensitivity is achievable for most chemical elements using small samples (in the microliter range). Through appropriate control of the electrical power and thus of the temperature of the atomizer, it is possible to separate most of the matrix components which interfere during the atomization and measurement of the atom components of interest (analyte residue). However, this effect cannot be eliminated completely.

This is also true for a method, which is shown in FIGS. 1 and 2 for which a technical solution disclosed in GDR WP 143,178 or German Offenlegungsschrift 3,600,943 is used. In this method, an analyte residue, after an electrothermal atomization $a_1$, is stimulated by a hollow cathode discharge $b_1$, which generally is already ignited and burning stably before the atomization. A measurement interval $c_1$ extends over the whole process. The background $b_1$ of the hollow cathode discharge, the continuum $C_1$ of the atomizer tube wall and the noise $D_1$ of the detection electronics as well as outside light are superimposed on the resulting analyte signals $A_1$ as interfering background signals.

It is known such a background as that the above background can be eliminated by making and change signal measurements in rapid succession alternately on the atomic emission line and on one or several of the adjacent wavelengths and subsequently forming the difference between the signals.

A similar method in atomic absorption spectroscopy provides for an alternating measurement of the narrow band extinction on the atom line and a broad band measurement of the background extinction. The effect of the background absorption is compensated for by forming the difference.

Further known methods make use of a modulated Zeeman splitting in the radiation source or in the sample space and subsequently form the difference between the two signals.

It is a disadvantage, especially in the variation for emission spectroscopy, that, aside from signal losses when fading out the spectral line, spectral lines lying next to this line can distort the background value. For a simultaneous multielement analysis, this method moreover, has the disadvantage that a wavelength shift depends on the thickness and refractive index of the tiltable plate used and on the reciprocal linear dispersion in the spectral order in question, in which the detection lines lie.

It is the object of the invention to ensure a high detectability and a high correctness of the measurement results with little effort.

The invention is directed to avoiding sample vapor losses and ensuring background compensation, in which the measurement of the analyte signal and the background signal takes place at the same wavelength and distortions of the background signal are largely excluded.

Pursuant to the invention, this objective is accomplished by a method for background compensation in material analysis, in which the value of a background signal is separated from the value of a gross analyte signal, which is generated by athermal radiation excitation after thermal vaporization of an analyte residue, by effecting the atomization in a step-like manner by stepwise heating and dividing each step into a first part for the measurement of the gross analyte signal and a second part for the measurement of the background signal.

The first measurement part is defined by a heating ramp, which generates the gross analyte signals having a magnitude which corresponds at least to twice the amount of the standard deviation of the background noise. The second measurement part is constructed as a temperature holding phase without atomization. To measure the signals in the two parts, identical measuring times are provided which correspond at least to the half-value width of the gross analyte signal.

The stepwise heating ensures an effective utilization or excitation by radiation of the atom vapor clouds of the analyte components formed by the atomization since there is no excess of neutral particles, which interfere with the hollow cathode discharge, as may be the case with simultaneous multielement analysis or high alkali contents.

It is advantageous if, in each section, a pulse-shaped hollow cathode discharge is effective, the pulse duration of which corresponds at least to the duration of the analyte vapor output during the atomization.

It is, moreover, advantageous if the gas pressure necessary for the hollow cathode discharge is increased synchronously with the heating steps and suddenly during the transition from the cold to the arc-like hollow cathode discharge.

Due to the periodic ignition of the hollow cathode discharge, spectral lines with a high excitation potential are effectively stimulated. For this reason and due to the stepwise increase in gas pressure, it is, moreover, possible to carry out a gas exchange while the hollow cathode discharge is not burning and to ensure gas-stop-like conditions for the duration of the hollow cathode discharge. As a result, the atom vapor clouds can be kept better at their place of origin.

It is moreover an object of the invention to provide an arrangement for implementing the method, in which the unit for thermal atomization and athermal excitation is connected to control units for temperature control, hollow cathode discharge and gas pressure control, as well as, via dispersing optical means, with detectors, the output signals of which are applied to a controllable integrator. A clock generator is connected to the control unit for the hollow cathode discharge and the integrator to control its function, as well as via a frequency divider to halve the clock frequency for the control units for temperature and gas pressure control and for the algebraic sign control of the integrator.

The invention will be explained in greater detail below by means of the schematic drawings, FIGS. 1 and 2 illustrate a prior art method.

The stepwise increase in the atomizer temperature $a_2$ is associated in each step in a first method part 1 with a vaporization of a portion of the analyte residue and a gross signal comprised of the net analyte signal $A_2$ and the background signal, is generated by the excitation $b_2$. The components of the background signal are formed by the discharge background $B_2$ of the hollow cathode discharge $B_2$, by the continuum $C_2$ of tube wall serving for the atomization and by the noise $D_2$ of the detection electronics or by outside light. A second, connecting method part 2 is defined by a temperature holding phase, in which the net analyte signal $A_2$ has decayed or can no longer be differentiated from the background. Synchronously with the method parts, measurements are scheduled in equal measurement intervals $c_2$, which correspond at least to the half-value width of the gross analyte signals and which determine from the first section a value $(A_2+B_2+C_2+D_2)_n$ and from the second section a value for $(B_2+C_2+D_2)_n$, n being the step number. The difference between these values is subsequently formed and a summation over all n forms the value of the complete net analyte signal.

The hollow cathode discharge and the gas pressure can either be switched on constantly and kept constant respectively in a known manner or adapted to the stepwise heating. With the latter procedure, a pulsatory hollow cathode discharge is effective as excitation $b_2$ in each of the two sections 1 and 2 and the gas pressure required for the hollow cathode discharge is increased in time with the heating steps. The increase is sudden during the changeover from the cold to the arc-like hollow cathode discharge.

Figure 1:
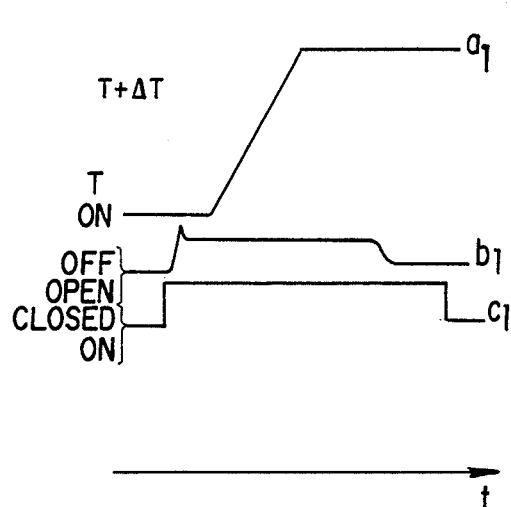
Figure 2:
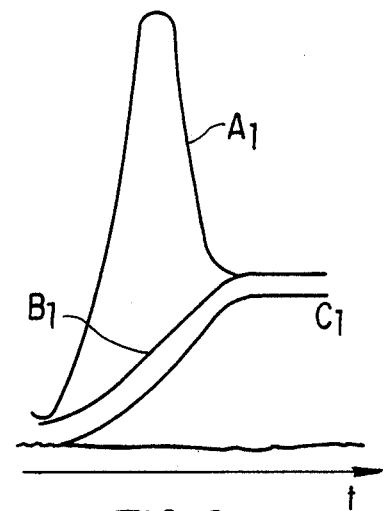
Figure 3:
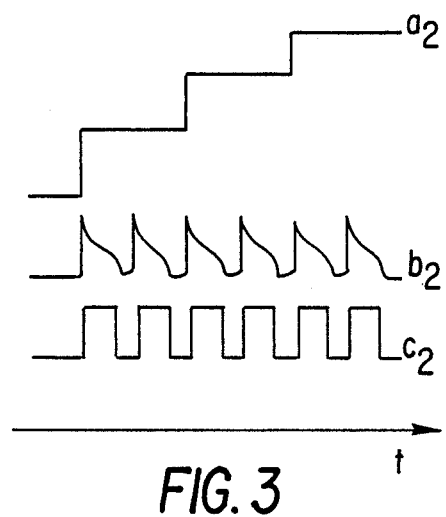
FIG. 3 shows curves which characterize the hollow cathode excitation $b_2$ as a pulsed operation in accordance with the invention.
Figure 4:
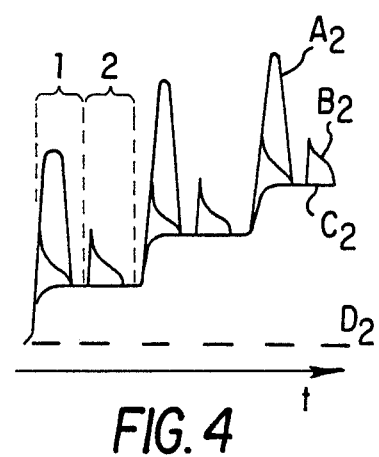
FIG. 4 shows the signals occurring in the steps.
Figure 5:
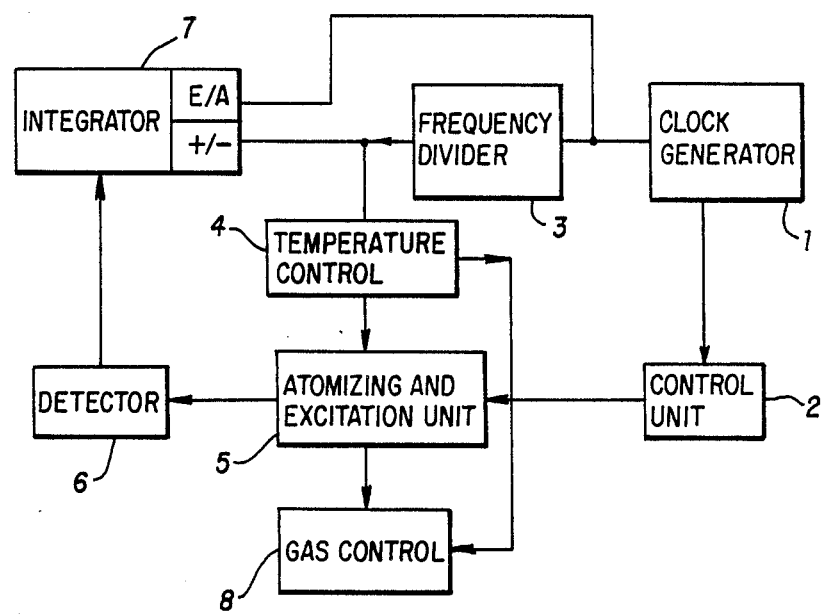
FIG. 5 shows a block circuit diagram of an arrangement for realizing the method described.

To realize the method of the invention, the hollow cathode is controlled according to FIG. 5 by a clock generator 1 via a control unit 2 with a first clock. At the same time, the frequency of the first clock emanating from the clock generator 1 is divided in a ratio of 1:2 by a frequency divider 3, so that a second clock results, which is applied to a temperature control 4 for an atomizing and excitation unit 5. A heating voltage is applied to the atomizer tube in the atomizing and excitation unit 5 to increase the temperature only during the active phase of the second clock. In the wattless off-phase of the second clock, which determines the temperature holding phase, in which the temperature may, however, also drop slightly, there is no atomization. With that, the stepwise heating and consequently the stepwise atomization of the analytes is attained. A gas control 8, which is connected with the atomizing and excitation unit 5, is also acted upon by the second clock.

The optical output signal of the atomizing and excitation unit 5 passes through a dispersing optical system (not shown) and reaches a detector 6, the electrical output signal of which is applied to a controllable integrator 7. The first clock of the clock generator is applied to the input of the integrator 7 in order to release it. Consequently, the signal is integrated only while the hollow cathode discharge is burning. The algebraic sign of the integration is controlled by the second clock. By these means, the value of the background signal $(B_2+C_2+D_2)_n$ is subtracted from the gross analyte signal $(A_2+B_2+C_2+D_2)_n$ and the net analyte signal $A_2$ is produced. The first clock advantageously is timed so as to be synchronized with the power supply, so that the second clock comprises a more or less complete clock period. By these means, the transformer for the heater voltage is relieved of d.c. components.

The controllable integrator 7 can be realized with little effort, if the detectors 6 are connected in series with a current and voltage frequency converter and a controllable backwards and forwards counter, the release of which is controlled by the first clock and the counting direction of which is controlled by the second clock.

We claim:

1. In a method for background compensation in material analysis, in which the value of the background signal is separated from the value of a gross signal of an analyte, said gross signal being generated after thermal atomization of an analyte residue by athermal excitation, the improvement comprising thermally atomizing the analyte residue in a stepwise manner by stepwise heating and separating each step into a first portion for the measurement of the gross analyte signal and a second portion for the measurement of the background signal.

2. The method of claim 1, wherein the first method portion is defined by a heat ramp which produces gross analyte signals having a magnitude which corresponds at least to twice the amount of the standard deviation of the background noise and the second method portion comprises a temperature holding phase without atomization, the signals in the two measuring portions having identical measuring times which correspond at least to the half-value width of the gross analyte signal.

3. The method of claim 2, wherein during each measuring portion a pulse-shaped hollow cathode discharge is active having a pulse duration corresponding at least to the duration of the analyte vapor output.

4. The method of claim 3, wherein the gas pressure for the hollow cathode discharge is increased synchronously with the heating steps and suddenly during the transition from a cold to an arc-like hollow cathode discharge.

5. In an arrangement for background compensation in material analysis, in which a unit for thermal atomization and athermal excitation is connected to control units for temperature control, hollow cathode discharge and gas pressure control as well as via dispersing optical means with detectors, the output signals of the detectors being applied to an integrator, the improvement wherein a clock generator is connected to the control unit for the hollow cathode discharge and the integrator to control the operation thereof, as well as via a frequency divider to halve the clock frequency to control the control units for temperature and gas pressure and to control the algebraic sign of the integrator.

* * * * *